(12) United States Patent
Raphael et al.

(10) Patent No.: US 11,067,573 B2
(45) Date of Patent: Jul. 20, 2021

(54) LIGHT MICROSCOPY CHIPS AND DATA ANALYSIS METHODOLOGY FOR QUANTITATIVE LOCALZIED SURFACE PLASMON RESONANCE (LSPR) BIOSENSING AND IMAGING

(71) Applicant: The Government of the United States of America, as represented by the Secretary of the Navy, Arlington, VA (US)

(72) Inventors: Marc P. Raphael, Washington, DC (US); Joseph A Christodoulides, Alexandria, VA (US); Jeff M Byers, Fairfax Station, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 639 days.

(21) Appl. No.: 15/882,081

(22) Filed: Jan. 29, 2018

(65) Prior Publication Data

US 2018/0164309 A1    Jun. 14, 2018

Related U.S. Application Data

(62) Division of application No. 14/039,288, filed on Sep. 27, 2013, now Pat. No. 9,915,654.

(51) Int. Cl.
*G01N 33/557*    (2006.01)
*G01N 21/552*    (2014.01)
*G01N 33/543*    (2006.01)

(52) U.S. Cl.
CPC ......... *G01N 33/557* (2013.01); *G01N 21/554* (2013.01); *G01N 33/54346* (2013.01); *G01N 33/54373* (2013.01); *G01N 33/54386* (2013.01)

(58) Field of Classification Search
CPC .............. G01N 33/557; G01N 21/554; G01N 33/54346; G01N 33/54373; G01N 33/551; G01N 33/553
(Continued)

(56) References Cited

PUBLICATIONS

Raphael et al, "A New Methodology for Quantitative LSPR Biosensing and Imaging", Anal. Chem., 2012, 84, 3, 1367-1373.*

\* cited by examiner

*Primary Examiner* — Christopher L Chin
(74) *Attorney, Agent, or Firm* — US Naval Research Laboratory; Rebecca L. Forman

(57) ABSTRACT

A chip for localized surface plasmon resonance (LSPR) biosensing and imaging having a glass coverslip compatible for use in a standard microscope and at least one array of functionalized plasmonic nanostructures patterned onto the glass coverslip with electron beam nanolithography. The nanostructures can be regenerated allowing the chip to be used multiple times. Also disclosed is a method for determining the fractional occupancy values for surface-bound receptors as a function of time for LSPR biosensing from the spectroscopic response of the array and modeling the photon count in each spectrometer channel, allowing for a functional relationship to be determined between the acquired spectrum and the fractional occupancy of binding sites on the array. Additionally disclosed is a method for the spatiotemporal mapping of receptor-ligand binding kinetics in LSPR imaging using the chip and projecting a magnified image of the array to a CCD camera and monitoring the binding kinetics of the array.

8 Claims, 9 Drawing Sheets

(58) Field of Classification Search
USPC .......... 422/82.11; 435/288.7, 808; 436/164, 436/517, 524, 525, 805
See application file for complete search history.

LIGHT MICROSCOPY CHIPS AND DATA ANALYSIS METHODOLOGY FOR QUANTITATIVE LOCALZIED SURFACE PLASMON RESONANCE (LSPR) BIOSENSING AND IMAGING

PRIORITY CLAIM

This application is a divisional application of U.S. application Ser. No. 14/039,288 filed on Sep. 27, 2013 by Marc P. Raphael et al., entitled "LIGHT MICROSCOPY AND DATA ANALYSIS METHODOLOGY FOR QUANTITATIVE LOCALZIED SURFACE PLASMON RESONANCE (LSPR) BIOSENSING AND IMAGING," which claimed priority from U.S. Provisional Application No. 61/706,911 filed on Sep. 28, 2012 by Marc P. Raphael et al., entitled "LIGHT MICROSCOPY AND DATA ANALYSIS METHODOLOGY FOR QUANTITATIVE LOCALZIED SURFACE PLASMON RESONANCE (LSPR) BIOSENSING AND IMAGING" and U.S. Provisional Application No. 61/839,428 filed on Jun. 26, 2013 by Marc P. Raphael et al., entitled "SILICON BACKING RING AND MULTIPLEXING APPLICATIONS FOR LSPR IMAGING." The entire contents of each of these cited applications and all references cited throughout this application and each of these cited applications are incorporated herein by reference.

CROSS REFERENCE

Cross reference is made to copending application Ser. No. 14/039,326, filed Sep. 27, 2013, entitled "CALIBRATING SINGLE PLASMONIC NANOSTRUCTURES FOR QUANTITATIVE BIOSENSING," by Marc P. Raphael, et al., the disclosure of which is incorporated herein by reference in its entirety.

BACKGROUND OF THE INVENTION

Field of the Invention

The present invention relates to light microscopy-based chips and quantitative analysis methodology for localized surface plasmon resonance (LSPR) biosensing and imaging.

Description of the Prior Art

Localized surface plasmon resonance (LSPR) is an emerging technique in the field of label-free biosensing which is currently dominated by the closely related, but more mature surface plasmon resonance (SPR) technique. (P. Englebienne, *Analyst,* 123, 1599-1603 (1998); A. J. Haes et al., *J. Am. Chem. Soc.,* 124, 10596-10604 (2002); N. Nath et al., *Anal. Chem.,* 74, 504-509 (2002); B. Sepulveda et al., *Nano Today,* 4, 244-251 (2009); J. Zhao et al., *Nanomedicine,* 1, 219-228 (2006)). Both employ the coupling of light with metallic structures for the excitation of a plasmonic resonance and both take advantage of the fact that the resonance is sensitive to changes in the index of refraction near the metallic surface and thereby can be used to detect the presence of analytes such as proteins or nucleic acids. In SPR, total internally reflected light, typically introduced by a prism, is incident at the "resonant" angle that excites surface plasmon polaritons propagating laterally along a planar, thin metal film. The sensitivity of the resonance to the presence of analytes extends hundreds of nanometers above the thin film's surface. (L. S. Jung et al., *Langmuir,* 14, 5636-5648 (1998) and K. Kurosawa et al., *Phys. Rev. B,* 33, 789-798 (1986)). By contrast, the localized nature of the LSPR nanostructures, typically 50 to 150 nm in diameter, allows for a range of incident light angles to be utilized, from normal to totalinternally reflected, and the sensitivity to analyte is confined to within tens of nanometers from the surface. (M. D. Malinsky et al., *J. Am. Chem. Soc.,* 123, 1471-1482 (2001)).

Both techniques can be used for imaging, such that spatial and temporal information of analyte binding is acquired, although the concept of LSPR imaging offers some distinct advantages over that of SPR imaging. First, because the spatial resolution of LSPR is restricted only by the size of the nanoparticle, the imagery is in principle diffraction limited and indeed spectroscopic-based biosensing with single nanostructures has already been achieved. (K. M. Mayer et al., *Nanotechnology,* 21 (2010) and G. J. Nusz et al., *Anal. Chem.,* 30, 984-989 (2008)). By contrast, traditional SPR configurations have a lateral spatial resolution that is limited by the decay length of the surface plasmon polaritons, which is on the order of microns for the gold thin films typically employed. (C. E. Berger et al., *Anal. Chem.,* 70, 703-706 (1998) and B. Rothenhausler et al., *Nature,* 332, 615-617 (1988)). In addition, the fact that SPR is sensitive to dielectric variations hundreds of nanometers above the metallic surface can result in a convolution of solution- and surface-based changes. Finally, the ability to excite LSPR resonances at a range of incidence angles allows for the straightforward incorporation into commercially available wide-field microscopes employing high numerical apertures whereas SPR imaging configurations must be custom built.

In order to realize its promise and overtake the older SPR technology, methodologies for LSPR biosensing must be developed that allow for quantitative determination of important physical quantities such as the fractional occupancy of receptor sites at the surface. Ideally these measurements would be made on a platform also capable of LSPR imaging so that both spatial and temporal information could be gained simultaneously. The fractional occupancy of binding sites, f, is of particular interest because it can be used to calculate the analyte concentration at the sensor surface if the reaction rate constants are known or, conversely, to determine the rate constants if the analyte concentration is known.

BRIEF SUMMARY OF THE INVENTION

The present invention provides a chip for localized surface plasmon resonance (LSPR) biosensing and imaging having a glass coverslip compatible for use in a standard microscope and at least one array of functionalized plasmonic nanostructures patterned onto the glass coverslip with electron beam nanolithography. Also disclosed is a method for determining the fractional occupancy values for surface-bound receptors as a function of time for LSPR biosensing and imaging using the chip and spectroscopically charactering the array, modeling the photon count in each spectrometer channel, and functionally relating the acquired spectrum to a fractional occupancy of binding sites. Additionally disclosed is a method for the spatiotemporal mapping of receptor-ligand binding kinetics in LSPR imaging using the chip and projecting a magnified image of the array to a CCD camera and monitoring the binding kinetics of the array.

The purpose of the invention is to devise a light microscopy-based instrumental and quantitative analysis methodology for LSPR biosensing that determines surface-receptor fractional occupancy, as well as an LSPR imaging technique for the spatio-temporal mapping of binding events. There is currently no alternative method for measuring the fractional occupancy of surface-bound receptors, with the space and time resolution presented herein, on a commercially-available light microscopy platform that is also compatible with fluorescence and differential interference contrast (DIC) microscopy.

This application of LSPR biosensing and imaging has several advantages: (1) measurements are made in real-time, (2) the nanostructures are lithographically patterned onto standard glass coverslips enabling more traditional imaging techniques such as fluorescence and bright field imagery to be readily integrated, and (3) the nanostructures are calibrated for the quantitative determination of concentration as a function of time and space.

These and other features and advantages of the invention, as well as the invention itself, will become better understood by reference to the following detailed description, appended claims, and accompanying drawings.

BRIEF DESCRIPTION OF THE DRAWINGS

FIG. 7(a) shows raw data, and FIG. 7(b) shows normalized data.

DETAILED DESCRIPTION OF THE INVENTION

Figure 1:
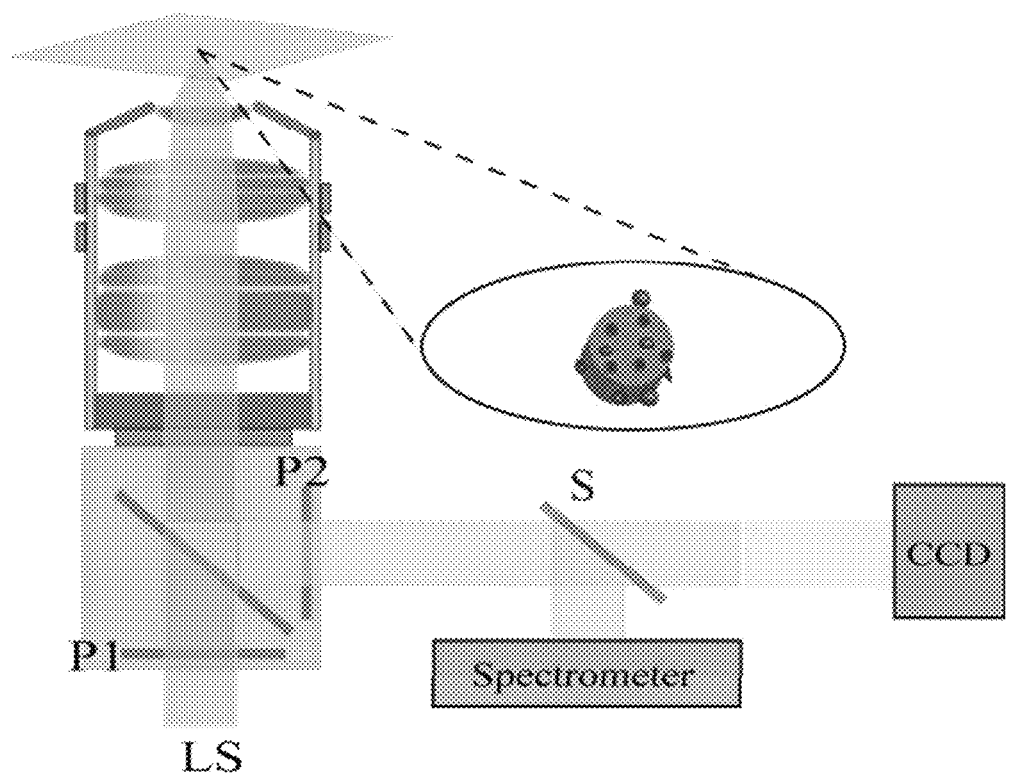
FIG. 1 is an illustration of the portion of the light train used for the excitation of the biofunctionalized gold nanostructures as well as the simultaneous detection of spectra and CCD imagery. P1 and P2 are crossed polarizers, S is a 50/50 beam splitter and LS is the light source. An illustration of a biofunctionalized gold nanostructure located atop the glass surface is shown as well in which the darker structures represent the receptors and the lighter structures represent the analytes.

The present invention provides a methodology for the determination of the time-dependence of the surface-receptor fractional occupancy, f(t), based upon LSPR spectroscopic measurements using an array of functionalized gold plasmonic nanostructures. The nanostructures were patterned by electron-beam nanolithography (EBL) into 20×20 arrays and each array as a whole characterized spectroscopically in a reflected geometry on an inverted light microscope. The data analysis methodology of the present invention models the photon count in each spectrometer channel as the sum of a baseline scattering rate and a scattering term sensitive to the small dielectric perturbations due to the binding of biomolecules at the surface of the nanostructures. This non-linear least squares approach to the data analysis sums over hundreds of these channels, at each point in time, giving it a distinct statistical advantage over a single channel approach, such as monitoring the peak wavelength. In this way, each acquired spectrum can be functionally related to a fractional occupancy of binding sites, f(t). One embodiment of the invention is the ability to measure, for the first time with LSPR, the binding kinetics of f(t) with the biotin-neutravidin binding pair and compare the obtained occupancy rates when varying the neutravidin concentration in solution from 50 nM to 1 μM. Another embodiment of the invention is a technique for regenerating the gold nanostructure arrays so that the same array of nanostructures can be used for repeated calibration and fractional occupancy measurements. This eliminates the uncertainties that can be introduced by the variability in the fabrication process when comparing results from different arrays. It is also unique in that it allows for fractional occupancy measurements in experiments in which the array is not saturated, provided it has been calibrated in a previous experiment or at the end of the current experiment. A further embodiment of the invention is a technique for the spatio-temporal measurements of analyte binding, obtained by projecting the magnified image of the array on to a charge coupled device (CCD) camera. Binding kinetics can be followed with a temporal resolution of 200 ms and a spatial resolution defined by the area of the array which was 8 m². A unique feature of these embodiments is that both the spectroscopic and the imaging application can be performed simultaneously. Also unique is that the experiments take place on a commercially-available inverted light microscope so that the techniques can be integrated with other more established light-microscopy techniques such as fluorescence and differential interference contrast (DIC).

Description of Materials Used

Biosensing

SH—$(CH_2)_{11}$-$EG_3$-$NH_2$ (SPN) and SH—$(CH_2)_8$-$EG_3$-OH (SPO) were purchased from Prochimia (Poland). Anhydrous 200 proof ethanol was purchased from Sigma-Aldrich (Milwaukee, Wis.). NHS-biotin, neutravidin (NA) and 10 mM phosphate buffered saline consisting of 140 mM NaCl and 10 mM KCl, pH 7.4 (PBS) were purchased from Thermo Scientific (Rockford, Ill.). No. 1.5, 25.4 mm diameter borosilicate glass coverslips were purchased from Warner Instruments (Hamden, Conn.). Ultrapure 18.2 M$\Omega$ deionized distilled water (DDW) was used as purified by a Milli-Q system from Millipore Ltd.

Electron-Beam Lithography

The electron-beam (e-beam) resists used were polymethyl methacrylate 4% in anisole (PMMA A4) and 6% ethyl lactate methyl methacrylate copolymer in ethyl lactate (MMA EL6), both purchased from Microchem (Newton, Mass.). The chromium etchant CR-7 was purchased from Cyantek (Fremont, Calif.) which is a concentrated perchloric acid-based etchant consisting of 9% $(NH_4)_2Ce(NO_3)_6$)–6% $HClO_4$+$H_2O$. Methyl isobutyl ketone (MIBK)+isopropyl alcohol (IPA) in a 1:2 ratio were used for developing the e-beam resists.

Nanostructure Array Fabrication

The substrates used for patterning the nanostructures were 25 mm diameter glass coverslips with a nominal thickness of 170 µm. Typical pretreatment of the substrates included soaking in piranha acid (3:1 $H_2SO_4$: $H_2O_2$) for a minimum of 5 hours and then washing with copious amounts of DDW. [Caution: piranha solution reacts violently with organic materials; it must be handled with extreme care, followed by rinsing with copious amounts of DDW]. A 10 nm chromium thin film was deposited prior to spinning the e-beam resists in order to eliminate charging during patterning of the nanostructures and when imaging them after lift-off. Substrates were then rinsed with acetone followed by IPA and baked on a hot plate to dehydrate the surface and promote resist adhesion. A bilayer process was used to facilitate lift-off. In this process, an undercut of the bottom layer was created to promote discontinuity of the deposited metal film. The copolymer used, MMA-EL6, is closely related to PMMA and spins on with a thickness of 180 nm at 2000 rpm. Next, PMMA A4 resist was spun at 3000 rpm to a thickness of 250 nm. Samples were then patterned via EBL using area doses in the range of 200 to 400 µC/cm$^2$ and various beam deflection profiles in order to adjust the size and shape of the nanostructures. The samples were developed for 1 minute in a MIBK:IPA bath. The chromium layer was wet-etched from the bottom of the pattern using CR-7 etchant. A Ti/Au layer was deposited using a Temescal electron-beam evaporator. Following the metal deposition, the PMMA/copolymer bilayer was lifted off by soaking in acetone for 4 hours. After SEM inspection of the arrays, the remaining chromium was removed, leaving Au nanostructures atop a glass substrate.

The nanostructures were patterned in arrays of 20×20 structures with each chip having 68 arrays. The pitch of the nanostructures within the arrays varied between 300 and 1000 nm and the size of the patterned nanostructures varied from 50 to 150 nm. In addition, a number of different nanostructure shapes were investigated, including rectangles, squares, discs and ovals.

Nanostructure Functionalization and Characterization

Cleaning

Sample regeneration was obtained by plasma ashing in 300 mTorr of a 5% hydrogen, 95% argon mixture for 45 seconds in a 40 watt RF plasma (Technics Series 85 reactive ion etcher (RIE)). The efficacy of this procedure in removing thiols and other organics from the nanostructure's surface was confirmed by X-ray Photoelectron Spectroscopy (XPS) studies on 80 nm thick planar gold thin films used as proxies for the nanostructures. The thin films samples were functionalized and exposed to protein using protocols that were identical to those employed on the nanostructures. High resolution XPS scans (Thermo Scientific K-Alpha XPS) were taken of the sulfur S 2p peak and nitrogen N 1s peak centered about 400 eV and 162 eV respectively, using a pass energy of 20 eV from an Al K$\alpha$ x-ray source focused to ~400 µm spot size. After plasma ashing, no sulfur was detected and the nitrogen signal observed on protein-coated samples was eliminated.

Biofunctionalization

Immediately following plasma ashing, the samples were incubated in 0.5 mM of 3:1 SPN/SPO ethanolic solution for 18 hours in order to form a self-assembled monolayer (SAM) on the gold nanostructures. The samples were then rinsed with ethanol and dried with nitrogen gas. For biotinylation, 0.3 mM of NETS-biotin in PBS was drop coated on to the sample for reaction with the amine terminus of the SPN. After a two hour incubation, the sample was rinsed with DDW and dried with nitrogen gas.

LSPR Microscopy and Spectroscopy

CCD-based LSPR imaging as well as LSPR spectra were collected in a reflected light geometry with an inverted microscope (Zeiss Axio Observer) using a 63×, 1.4 numerical aperture (NA) oil-immersion objective and Koehler illumination. Imagery and spectra were obtained simultaneously by placing a beam splitter at the output port of the microscope (see FIG. 1). The sample was epi-illuminated with polarized light from a 100 W halogen lamp and a crossed polarizer was used to reduce the background contribution from substrate-scattered light. For the spectral measurements, the focused image of the nanostructure array was projected on to the end of a 600 µm diameter optical fiber and the spectra were subsequently measured with a thermoelectrically-cooled, CCD-based spectrophotometer (Ocean Optics QE65000). The integration time was 5 seconds per spectrum. For image acquisition, the focused image of the array was projected on to a thermoelectrically-cooled CCD camera with 6.45 µm×6.45 µm sized pixels (Hamamatsu ORCA R$^2$) with frame integration times between 200 and 250 ms. Reference spectra were conveniently obtained by a 20 µm translation of the stage to an array-free spot on the sample. Dark spectra were obtained by shuttering the light source.

FIG. 1 is an illustration of the portion of the light train used for the excitation of the biofunctionalized gold nanostructures as well as the simultaneous detection of spectra and CCD imagery. P1 and P2 are crossed polarizers, S is a 50/50 beam splitter and LS is the light source. An illustration of a biofunctionalized gold nanostructure located atop the glass surface is shown as well in which the darker structures represent the receptors and the lighter structures represent the analytes.

The epi-illumination setup used to produce highly contrasted images of the gold nanostructures utilized a combination of Koehler illumination and crossed polarizers. First, the image of the Koehler illuminator field aperture was stopped down to a diameter of ~30 µm so that only the array of interest was illuminated, thus eliminating unwanted background contributions from the rest of the chip. Second, the condenser aperture was stopped down so that effective numerical aperture (NA) of illumination was less than 50% of the objective's total NA of 1.4. (As such, this configuration is the inverse of dark field illumination in that dark field illuminates exclusively at high NA and collects at a lower NA).

While these adjustments to the Koehler illuminator were adequate to obtain spectra there was still considerable background contribution due to scattering from the substrate. To reduce this background, polarized light was used for illumination and a crossed-polarizer to filter the collected light. The nanostructures are visible when using crossed-polarizers because of the dipole nature of their radiative emission. While directly backscattered light from the nanostructures and substrate will have the same polarization as the incident light and is thus filtered by the crossed polarizer, off-axis dipole emission will contain a component of the electric field which is perpendicular to the excitation polarization.

Figure 2:
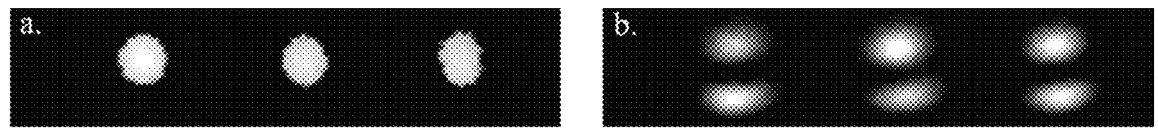
FIG. 2 shows three 80 nm diameter nanostructures imaged in (a) brightfield and (b) with crossed polarizers at a microscope magnification of 250×. The spacing between nanostructures was 1 μm. The medium was DDW, and the images were contrast enhanced for clarity.

For such an optical configuration, vector optics and Mie theory predict that the magnified image of a single nanostructure will form two bright lobes and indeed this is what is observed. FIG. 2a is a bright field image using unpolarized light of three nanostructures in DDW that are 80 nm in diameter. When viewed with crossed polarizers, each individual spot is replaced by two spots (FIG. 2b). The images were taken using a 100× objective with an additional 2.5× optivar lens for a total magnification of 250× and contrast enhanced for clarity.

Analyte was introduced under continuous flow conditions using a custom-made microfluidic cell with the 10 μL/min flow rate controlled by a syringe pump. The flow cell volume was 36 μL. The microscope stage was equipped with a temperature controlled insert and incubation chamber which kept the stage temperature and optical light train at 28.0±0.04° C. (PeCon GmbH). Under these conditions, the stage drift was less than 3 nm/min.

Selecting the Optimal Array for Analyte Detection

Figure 3:
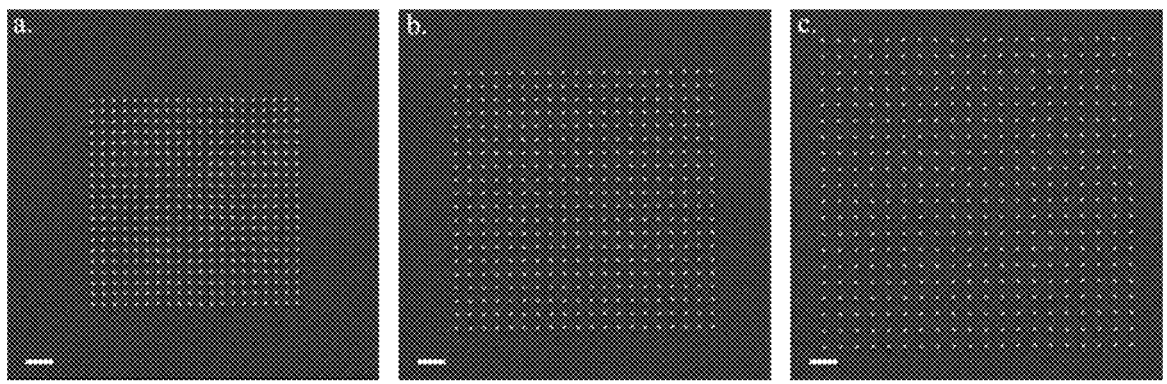
FIG. 3 shows SEM images of 20×20 arrays of varying pitch size: (a) 300 nm, (b) 400 nm, and (c) 600 nm. The images were taken on a witness sample in which the Cr under-layer was left in place for the sake of preventing charging problems in the SEM. All scale bars are 1 μm.
Figure 4:
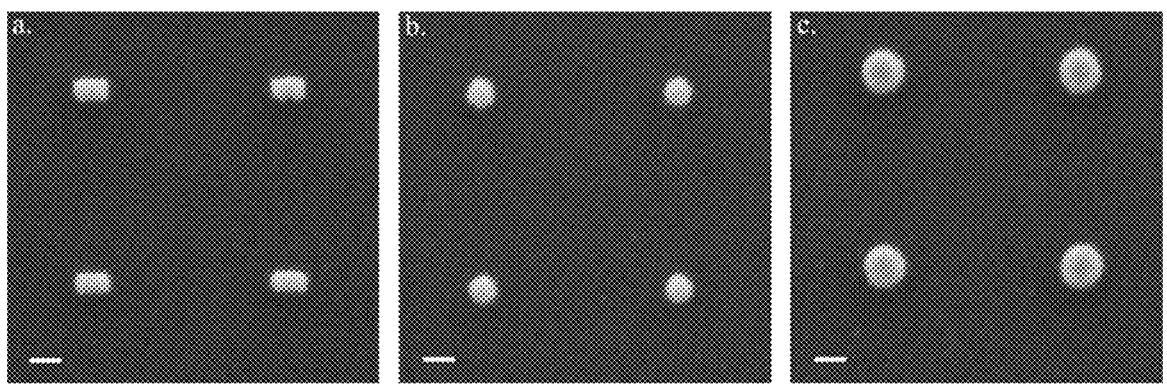
FIG. 4 shows SEM images of nanostructures of varying size and shape: (a) 110×65 nm rectangles, (b) 80 nm discs, and (c) 130 nm discs. The images were taken on a witness sample in which the Cr under-layer was left in place for the sake of preventing charging problems in the SEM. All scale bars are 100 nm.

EBL was used to pattern chips consisting of 68 arrays as described above. Each array consisted of 400 nanostructures in a 20×20 arrangement. The size, shape and pitch of the nanostructures were systematically varied from array to array in order to empirically determine the geometry that best matched the optical configuration. Shapes included circular, square, rectangular and elliptical cross sections as shown in FIGS. 3 and 4. The dimensions along the cross section were as small as 50 nm and as large as 150 nm; the height for all arrays was 80 nm. The pitch between nanostructures was varied from 300 nm to 1 μm. The images shown in FIGS. 3 and 4 were taken on a witness sample in which the Cr under-layer was left in place for the sake of preventing charging problems in the SEM.

The selection criteria for the array best suited for LSPR imaging was that the location of the LSPR peak lie between 600 nm and 700 nm in order to be well matched with the higher quantum efficiency (QE) range of the CCD camera. (For the wavelengths 650 nm, 750 nm, and 850 nm the QE of the camera was approximately 60%, 40%, and 20%, respectively.) It was found that nanostructures with approximate diameters or widths of 70±10 nm met this criteria while also having large enough scattering cross sections to allow for highly contrasted images to be obtained with camera exposure times of 250 ms or less.

Figure 5:
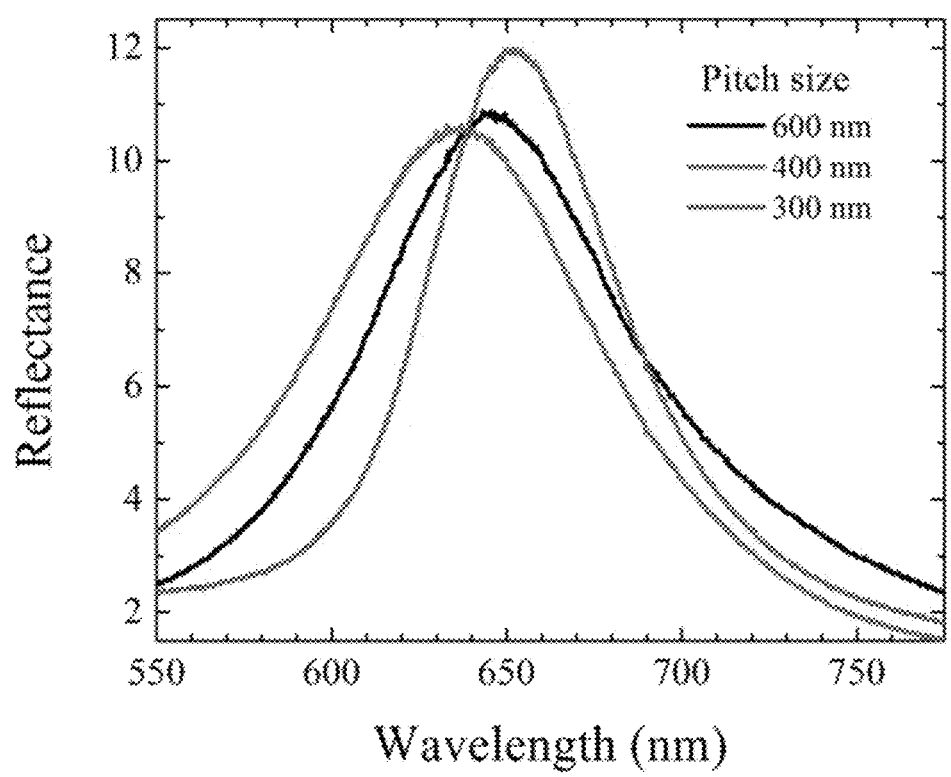
FIG. 5 shows LSPR peaks of three arrays with pitches of 300 nm (highest peak), 400 nm (shortest peak) and 600 nm (middle peak). All arrays consisted of ellipsoidal-shaped nanostructures with base dimensions of 70×75 nm. The spectra were taken in PBS, without flow.

After down-selecting for arrays based on the LSPR peak wavelength, the line widths of each array were compared by measuring the full width at half maximum as a function of pitch. In two-dimensional arrays of nanostructures, radiative coupling and interference of the scattered light can vary both the position of the resonance peak and its width. FIG. 5 compares the LSPR peak of three arrays containing ellipsoidal nanostructures with 70×75 nm bases but varying in pitch from 300 nm to 600 nm. The spectra were taken in PBS, without flow. The direction of incident light polarization was parallel to the minor axis of the ellipses. The reflectance was calculated as $$\text{reflectance} = \frac{N_{array}(\lambda) - N_{dark}(\lambda)}{N_{ref}(\lambda) - N_{dark}(\lambda)}$$

where $N_{array}$, $N_{dark}$ and $N_{ref}$ are the spectrometer counts for the array, dark, and reference spectra, respectively. The 300 nm pitch array showed a marked sharpening in the line width and was slightly shifted relative to the 400 and 600 nm pitched arrays. As a result, the 300 nm pitch array was used for all subsequent spectral- and image-based biosensing measurements.

Figure 6:
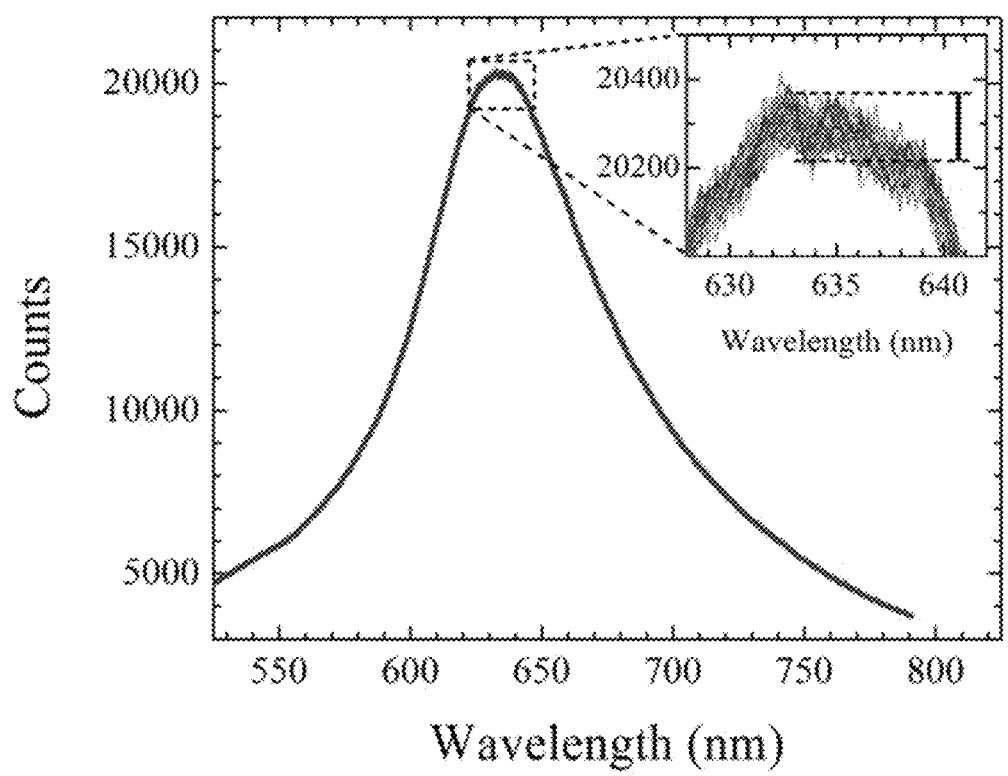
FIG. 6 shows a drift study: 172 spectra recorded over the course of one hour. The inset shows the data at the peak with a scale bar of length $(N)^{1/2}$, where N=20300, indicating the standard deviation from the counting statistics inherent in the spectrometer. The spectra were taken with PBS, flowing at a rate of 10 μL/min.

The data analysis methodology introduced below requires as input the number of counts in each of the spectrometer's data channels. A slowly varying, homogeneous drift across the entire spectrum is accounted for in the model but if the drift has a chromatic dependence, then the model can falsely associate it with the binding of analyte at the surface. At high optical magnifications, the most common causes of such variations are lateral stage drift, focus drift, and microfluidic-based perturbations. FIG. 6 shows a drift study in which 172 spectra were acquired over one hour. The spectra were taken with PBS, flowing at a rate of 10 μL/min. The inset allows for the visualization of the spread in the spectra by showing the data at the peak. The spread in counts at the peak is comparable to the square root of the number of counts (as indicated by the scale bar), demonstrating that for the setup the count uncertainty in a given channel is dominated by the counting statistics of the detector. The stability of the setup as demonstrated in FIG. 6 enabled the quantitative data analysis approach described below.

Figure 7:
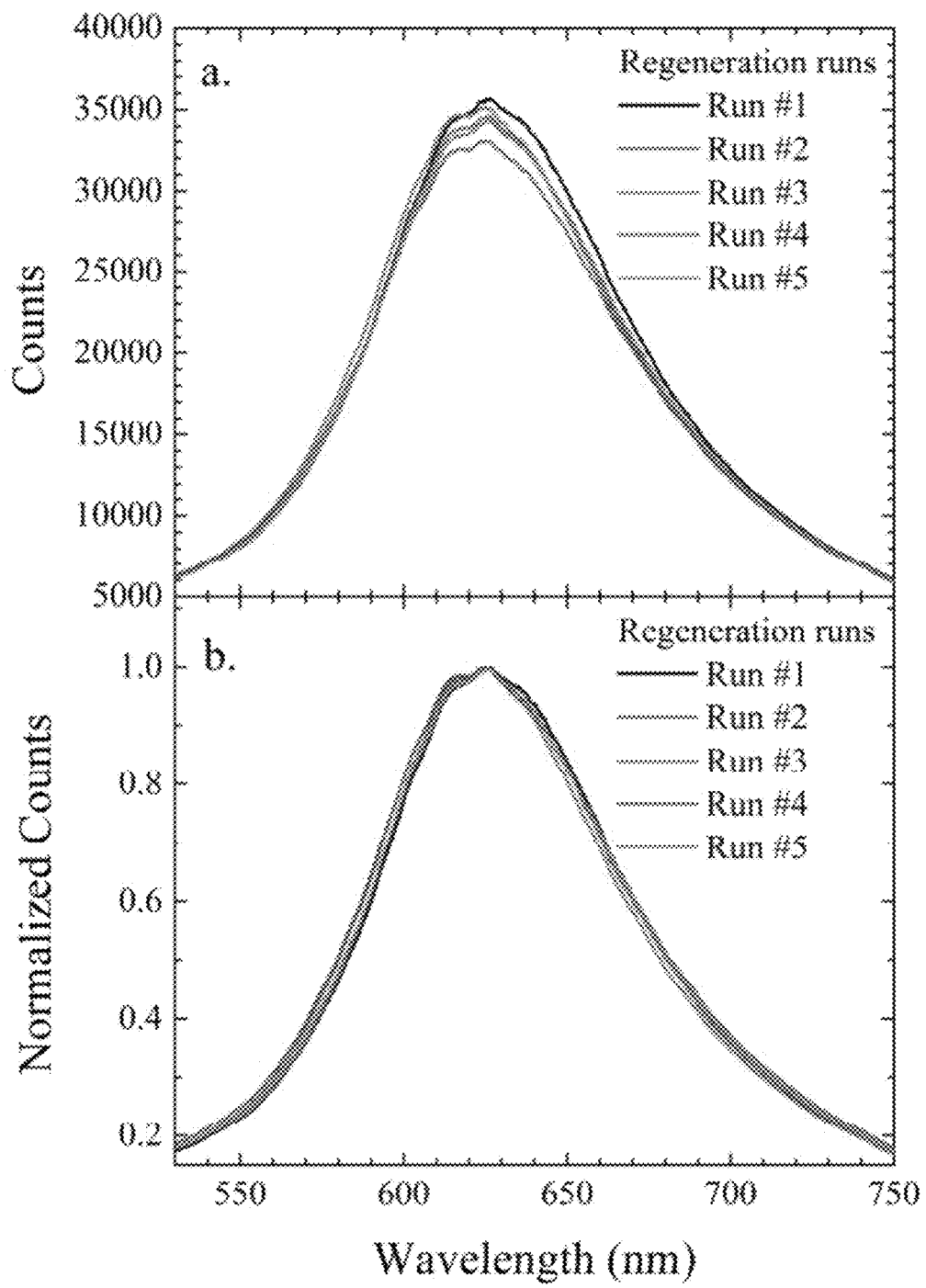
FIG. 7 shows spectra from five studies, each of which was proceeded by plasma ashing for the removal of all organics, followed by SAM layer deposition and subsequent biofunctionalization with biotin. All studies were conducted on the same array in PBS at a flow rate of 10 μL/min.

FIG. 7 shows that the spectra measured on a given array are reliably reproduced after repeated regenerations by plasma ashing, followed by biofunctionalization. If the plasma ashing had damaged the nanostructures, thus varying their size or shape, or the subsequent biofunctionalization steps were not reproducible, a variation in the LSPR peak position and width would be expected since both are known to be highly sensitive to such effects. FIG. 7 plots the spectra from five studies, taken on the same array in PBS at a flow rate of 10 μL/min, each of which was proceeded by plasma ashing for the removal of all organics, followed by SAM layer deposition and subsequent biofunctionalization with NHS-biotin as described in the Materials and Methods section. FIG. 7a shows the raw data in which intensity variations between studies are present. However, when normalized (FIG. 7b) the spectra are well reproduced. The differences between spectra in the raw data are likely due to day-to-day variations in the illumination intensity as well as slight differences in alignment when the chip is mounted on to the microscope. As will be shown below, the reproducibility displayed in FIG. 7b is necessary for the calibration of a given array to be reliably applied to subsequent data runs on the same array following the regeneration and biofunctionalization steps.

Data Analysis

To obtain the time-dependent fractional occupancy of receptors, f(t), we have taken a non-linear least squares approach to the data analysis. The mean photon count per spectrometer channel, acquired over the detector's integration time (τ), can be expressed as $$\overline{N}_i(t,t+\tau) = A_i \int_t^{t+\tau} dt' \, \Gamma_i(t') \qquad (1)$$

where $\overline{N}_i$, $A_i$ and $\Gamma_i$ are the mean photon count, the incident photon flux and the photon scattering rate, respectively. The photon scattering rate can be approximated by the sum of an initial scattering rate, $\Gamma_{0,i}$, a term sensitive to the dielectric perturbation of the bio-molecules, $\Gamma_{\epsilon,i}$, and a time-varying background term, $\Gamma_{B,i}$. Finite element simulations as well as dipole approximation modeling predict a linear dependence of the photon scattering rate to the fractional occupancy, $\Gamma_{\epsilon,i} \propto f$, in which case the scattering rate can be written as $$\Gamma_i(t) = \Gamma_{0,i} + \Gamma_{\epsilon,i} + \Gamma_{B,i} = \Gamma_{0,i} + \alpha_i f(t) + \beta_i g(t) \qquad (2)$$

where the background contribution is also assumed linear with respect to a separate function, g(t). Inserting these results into Eq. (1) yields $$\overline{N}_i(t,t+\tau) = \gamma_i \tau + a_i f(t) \cdot \tau + b_i g(t) \cdot \tau \qquad (3)$$

where $\gamma_i = A_i \Gamma_{0,i}$, $a_i = A_i \alpha_i$ and $b_i = A_i \beta_i$. The calibration data used to determine the values of the coefficients $\gamma_i$ and $b_i$ were obtained with no analyte present (f=0) while the calibration data for the determination of $a_i$ were obtained after the sensor had been saturated with neutravidin (f=1). Once obtained, these coefficients were applicable to all the specific and non-specific binding studies measured with the same array of nanostructures. An example of an f=0 spectrum versus an f=1 spectrum is shown in FIG. 6 in which the spectra were taken in PBS, flowing at a rate of 10 μL/min. We note that local topological features of the nanostructures such as defects, edges and surface roughness will create a complex dependence between the observed signal and the actual fractional occupancy at the nanoscale. For this reason, there was no attempt to measure and model individual nanostructures or even tens of nanostructures. Instead measurements were made on an ensemble of 400 nanostructures so that these local complexities are averaged out.

With the model thus established, the most probable values of f(t) are calculated using our non-linear least squares formalism in which the following log-likelihood function is minimized with respect to f $$\log_e[P(\vec{N} \mid f(t), g(t), \tau)] = const. - \frac{1}{2} \sum_{i=1}^{M} \frac{(N_i - \overline{N}_i)^2}{\sigma_i^2} \qquad (4)$$

where $N_i$ are the counts acquired in $i^{th}$ channel of a spectrometer with M total channels. As demonstrated in FIG. 6, the uncertainty in the number of counts in channel i is dominated by counting statistics, so that $\sigma_i^2 = N$. The error bars for the calculated f values are determined from the Gaussian co-variance matrix.

Spectroscopic and Imaging Based Kinetic Measurements

Figure 9:
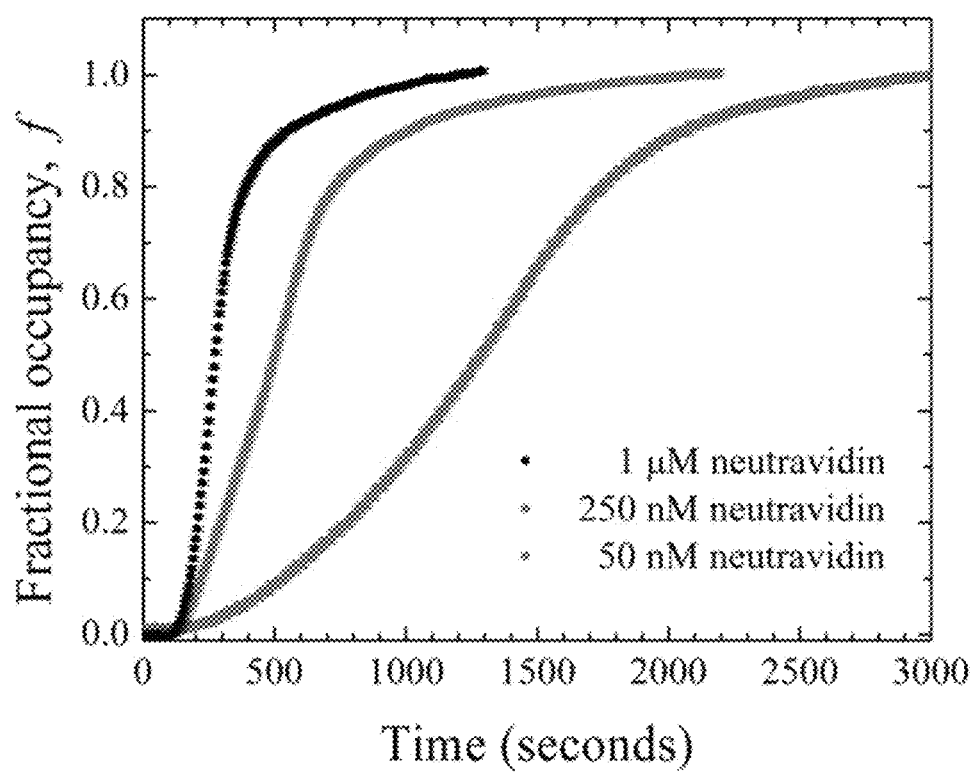
FIG. 9 shows neutravidin specific binding studies at 1 μM, 250 nM and 50 nM. The data were taken on the same array with the analyte in PBS, flowing at a rate of 10 μL/min. Between studies the array was subjected to plasma ashing for the removal of all organics, followed by the redeposition of the SAM layer and subsequent biofunctionalization with NHS-biotin.

In three separate experiments, neutravidin was introduced into the flow cell in concentrations of 1 μM, 250 nM and 50 nM. The time-dependent evolution of f for each concentration is shown in FIG. 9. The data were taken on the same array with the analyte in PBS, flowing at a rate of 10 μL/min. Between studies the array was subjected to plasma ashing for the removal of all organics, followed by the redeposition of the SAM layer and subsequent biofunctionalization with NHS-biotin.

Figure 8:
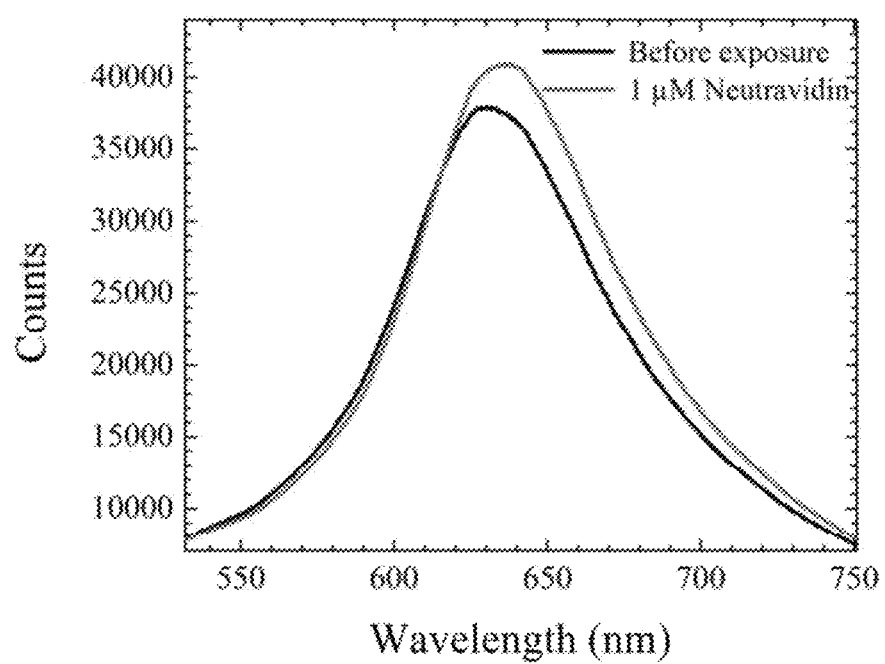
FIG. 8 shows LSPR spectra before (black) and after (gray) saturation with 1 μM of neutravidin. The spectra were taken with PBS, flowing at a rate of 10 μL/min.

In FIG. 9, f=1 was determined independently for each neutravidin concentration by assuming saturation at the end of the transition although a slight positive slope was measurable. To determine whether this slope was due to specific or non-specific binding, control studies were conducted in which the same experiments were repeated on the same array but without biotin conjugated to the SAM layer. As shown in FIG. 8 for the 250 nM neutravidin case, the slope at the end of the specific binding run is largely accounted for by non-specific binding and thus helps validate the f=1 assumption.

Figure 10:
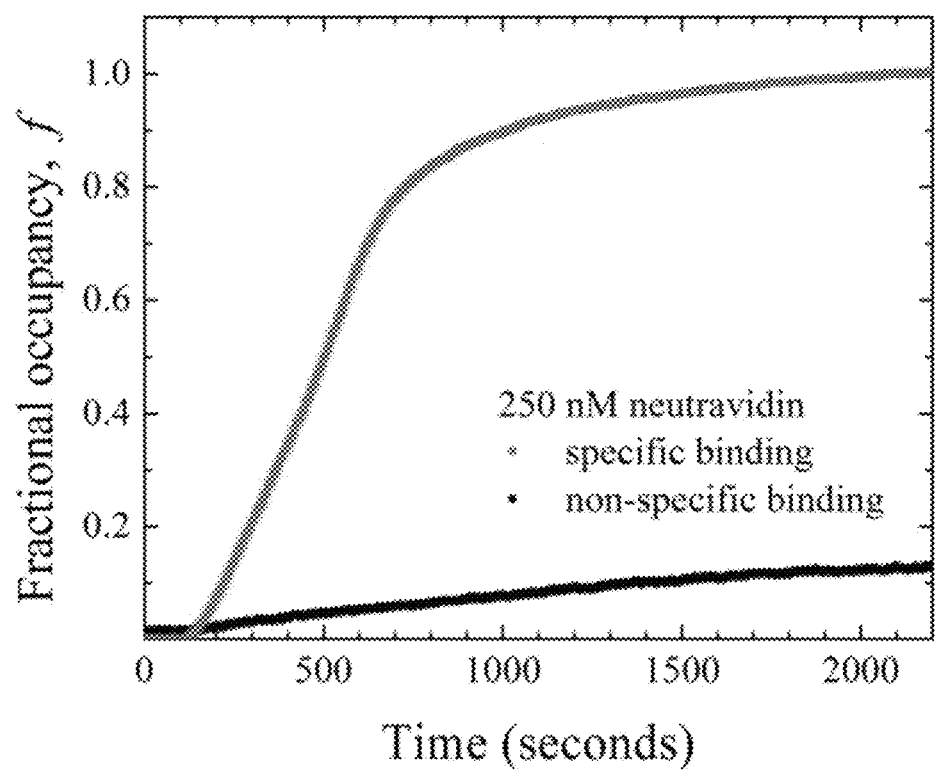
FIG. 10 shows specific (gray) vs. non-specific binding (black) for 250 nM neutravidin. For the non-specific study, no biotin was conjugated to the SAM layer. The data were taken on the same array in PBS, flowing at a rate of 10 μL/min.

The co-plot in FIG. 10 is possible because the calibration constants obtained from a previous saturation study, namely the 1 μM neutravidin study, were used in the analysis of the 250 nM non-specific binding data. The reliability of this procedure is dependent upon the spectroscopic features and sensitivity of the resonance peak being repeatable from one experiment to the next; a criterion achieved by regenerating and reusing the same array of nanostructures for all experiments (see FIG. 7*b*).

Figure 11:
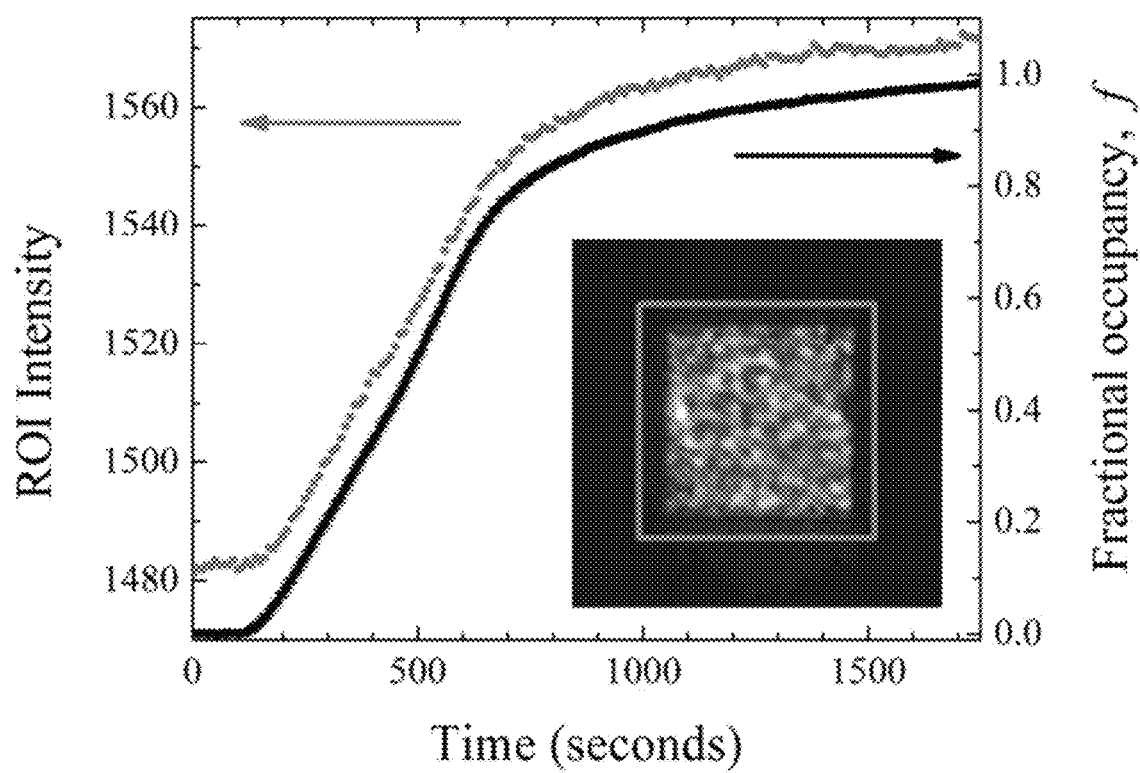
FIG. 11 shows LSPR imaging data (gray) versus spectroscopic data (black) for the 250 nM neutravidin specific binding study. The data were taken simultaneously on the same array with the analyte in PBS, flowing at a rate of 10 μL/min. The region of interest (ROI) intensity is the average intensity of the pixels bounded by the gray box in the inset image. The array size was 8×8 μm.

We now turn from the analysis of the spectroscopic data to the kinetics as measured simultaneously with the CCD camera. FIG. 11 plots the time course for the 250 nM neutravidin specific binding study as measured by the LSPR imaging technique and, for the sake of comparison, co-plots the analyzed spectroscopic data. Each LSPR imaging datum point is the average of the CCD pixel values contained within a region of interest (ROI) which incorporates the array of nanostructures (see FIG. 11 inset). As shown in FIG. 8, the binding of proteins to the surface of the gold nanostructures not only results in a shift of the resonance peak position but also in an increase in the scattering rate for the wavelengths between 610 nm and 750 nm. As a result, the image of the nanostructures brightens with increased fractional occupancy. FIG. 11 demonstrates that the LSPR imaging technique presented here has the sensitivity to monitor binding kinetics at the surface of the gold nanostructures for a 20×20 array. The time resolution has been enhanced from the 5 seconds spectrometer exposure time to 200 ms for the CCD camera exposure time as a result of the fact that the CCD pixel count is a sum over all the LSPR peak wavelengths, with each wavelength weighted by QE(λ) of the detector. Another important advantage of LSPR imaging is that it gives spatial information as well as temporal. The current study is restricted to a ROI that incorporates the entire array, an area of 8 μm².

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed as new and desired to be protected by Letters Patent of the United States is:

1. A method for determining fractional occupancy values for surface-bound receptors as a function of time for localized surface plasmon resonance (LSPR) biosensing and imaging, comprising:

using a chip for LSPR biosensing, comprising a glass coverslip compatible for use in a standard microscope, wherein at least one array of functionalized plasmonic nanostructures for LSPR biosensing and imaging has been patterned onto the glass coverslip with electron beam nanolithography, wherein the functionalized plasmonic nanostructures are calibrated for a quantitative determination of concentration as a function of time and space;

projecting a focused image of the array to spectroscopically characterize the array;

modeling the photon count in each spectrometer channel as the sum of a baseline scattering rate and a scattering term sensitive to small dielectric perturbations, wherein the modeling can sum hundreds of spectrometer channels at each point in time; and functionally relating an acquired spectrum to a fractional occupancy of binding sites using a non-linear least squares calculation.

2. The method of claim 1, wherein the functionalized plasmonic nanostructures comprise functionalized gold plasmonic nanostructures.

3. The method of claim 1, wherein the array comprises 20×20 nanostructures.

4. The method of claim 1, wherein the pitch between the arrays is in the range from 150 to 1000 nm.

5. The method of claim 1, wherein the size of the patterned nanostructures is in the range from 50 to 150 nm.

6. The method of claim 1, wherein the shape of the nanostructures comprises rectangles, squares, discs, ovals, or any combination thereof.

7. The method of claim 1, wherein the nanostructure arrays can be regenerated.

8. The method of claim 7, wherein the nanostructure arrays are regenerated by plasma ashing.

* * * * *